US011189381B2

(12) United States Patent
Gondhalekar et al.

(10) Patent No.: US 11,189,381 B2
(45) Date of Patent: Nov. 30, 2021

(54) MOVING-HORIZON STATE-INITIALIZER FOR CONTROL APPLICATIONS

(71) Applicant: The Regents of the University of California, Oakland, CA (US)

(72) Inventors: Ravi L. Gondhalekar, Cambridge, MA (US); Francis J. Doyle, III, Cambridge, MA (US); Eyal Dassau, Cambridge, MA (US)

(73) Assignee: The Regents of the University of California, Oakland, CA (US)

( * ) Notice: Subject to any disclaimer, the term of this patent is extended or adjusted under 35 U.S.C. 154(b) by 507 days.

(21) Appl. No.: 15/990,634

(22) Filed: May 27, 2018

(65) Prior Publication Data
US 2018/0277253 A1    Sep. 27, 2018

Related U.S. Application Data

(63) Continuation of application No. 15/424,824, filed on Feb. 4, 2017, now Pat. No. 9,984,773, which is a continuation of application No. PCT/US2015/043763, filed on Aug. 5, 2015.

(60) Provisional application No. 62/034,132, filed on Aug. 6, 2014.

(51) Int. Cl.
| *A61M 5/172* | (2006.01) |
| *G16H 50/50* | (2018.01) |
| *G16H 40/63* | (2018.01) |
| *G16Z 99/00* | (2019.01) |
| *G16H 20/17* | (2018.01) |
| *A61M 5/142* | (2006.01) |

(52) U.S. Cl.
CPC .......... *G16H 50/50* (2018.01); *A61M 5/1723* (2013.01); *G16H 20/17* (2018.01); *G16H 40/63* (2018.01); *G16Z 99/00* (2019.02); *A61M 2005/14208* (2013.01); *A61M 2205/18* (2013.01); *A61M 2205/50* (2013.01); *A61M 2230/201* (2013.01)

(58) Field of Classification Search
CPC ........... A61M 2230/201; A61B 5/1495; A61B 5/14532; G16H 50/50
See application file for complete search history.

(56) References Cited

U.S. PATENT DOCUMENTS

| 9,451,908 | B2 * | 9/2016 | Kamath | ............... A61B 5/6848 |
| 2008/0086273 | A1 * | 4/2008 | Shults | .................. A61B 5/1473 702/19 |
| 2010/0057042 | A1 * | 3/2010 | Hayter | ................. A61B 5/7275 604/504 |
| 2010/0057044 | A1 * | 3/2010 | Hayter | ................ A61M 5/1723 604/504 |
| 2010/0295686 | A1 * | 11/2010 | Sloan | ..................... G16H 20/17 340/573.1 |

(Continued)

*Primary Examiner* — Kibrom K Gebresilassie
(74) *Attorney, Agent, or Firm* — Richard Aron Osman

(57) ABSTRACT

A state-estimator for the estimation or initialization of the state of a discrete-time state-space dynamical model based on sensor measurements of the model output, comprising fitting a continuous-time function to acquired sensor measurement data-points of each model output, and subsequently sampling the continuous time function at exactly the sample-period of the state-space dynamic model for which the state is being estimated or initialized, in order to construct a model state via a synthesized output trajectory.

18 Claims, 4 Drawing Sheets

(56) References Cited

U.S. PATENT DOCUMENTS

| | | | | |
|---|---|---|---|---|
| 2010/0298765 A1* | 11/2010 | Budiman | ............. | A61B 5/4839 |
| | | | | 604/66 |
| 2011/0029269 A1* | 2/2011 | Hayter | ................ | A61M 5/1723 |
| | | | | 702/104 |
| 2012/0215087 A1* | 8/2012 | Cobelli | ................ | A61B 5/1495 |
| | | | | 600/365 |
| 2013/0085679 A1* | 4/2013 | Budiman | ............... | G16B 99/00 |
| | | | | 702/19 |
| 2013/0179108 A1* | 7/2013 | Joseph | .................... | G06F 3/046 |
| | | | | 702/104 |
| 2014/0273042 A1* | 9/2014 | Saint | ................. | A61B 5/14532 |
| | | | | 435/14 |
| 2015/0289820 A1* | 10/2015 | Miller | .................. | A61B 5/4875 |
| | | | | 600/300 |
| 2016/0058343 A1* | 3/2016 | Di Cristina | .......... | A61B 5/1473 |
| | | | | 600/347 |

* cited by examiner

MOVING-HORIZON STATE-INITIALIZER FOR CONTROL APPLICATIONS

CROSS-REFERENCE TO RELATED APPLICATIONS

This application is a continuation of Ser. No. 15/424,824, filed: Feb. 4, 2017, now U.S. Pat. No. 9,984,773; which is a continuation of PCT/US15/43763; filed: Aug. 5, 2015, which claims priority to 62/034,132; filed: Aug. 6, 2014.

This invention was made with government support under Grant Numbers DP3DK094331 and ROIDK085628 awarded by the National Institutes of Health (NIH). The government has certain rights in the invention.

INTRODUCTION

The overall goal of our research and development is an Artificial Pancreas (AP) for automated insulin delivery to people with Type 1 Diabetes Mellitus (T1DM) (see, e.g., Cobelli et al. [2009], Harvey et al. [2010], Cobelli et al. [2011], Zisser [2011], Doyle III et al. [2014]). In particular, an AP with glucose sensing (measurement for feedback) by a Continuous Glucose Monitor (CGM) (Hovorka [2006]) is considered. A crucial element of an AP is a feedback control law that performs algorithmic insulin dosing that is effective and safe. For example, glycemia controllers based on Model Predictive Control (MPC) (Parker et al. [1999], Hovorka et al. [2004], Magni et al. [2009], Breton et al. [2012], Turksoy et al. [2013]) have been proposed. Our group is focusing increasingly on developing so-called zone-MPC strategies (Grosman et al. [2010, 2011], van Heusden et al. [2012], Gondhalekar et al. [2013, 2014].

A critical ingredient of every MPC implementation is a mechanism to characterize an initial condition from which to perform predictions. Two main approaches exist. In MPC based on general state-space models, a state estimator is typically employed, e.g., a Luenberger-observer or Kalman-filter (see, e.g., Levine [2011]). Alternatively, when using input-output models, e.g., an Auto-Regressive model with eXogenous inputs (ARX), the initial condition consists trivially of past input and output values (even when using the system's state-space representation). The state estimator approach is favored by us even for ARX model-based predictive control, because it provides simple handles for tuning noise-rejection capabilities. The input-output approach is employed in, e.g., Magni et al. [2007], where it is stated that "The major advantages of this input-output MPC scheme are that an observer is not required". Both recursive linear state estimators (the class subsumes Luenberger-observers and standard Kalman-filters) and the input-output initialization are straightforward to implement, but have weaknesses. This work addresses at least three of these weaknesses. A device that initializes MPC predictions is henceforth simply termed a state estimator, regardless of the model class. The provided state estimator is applicable to both general state-space models as well as input-output models.

The first weakness addressed herein is that sensor recalibrations cannot be accommodated well in current state estimators. CGM signals suffer two (at least) types of noise. First, there is high-frequency stochastic noise, the effects of which can, to some extent, be remedied by tuning the gain of a recursive state estimator (Bequette [2004]). Then there is a low-frequency drift, also termed sensor bias, due to slowly undulating characteristics of the CGM sensor gain and changes in the sensor site's physiology. These low-frequency disturbances are corrected by taking sporadic blood-glucose measurements with a sensor that is more accurate than the CGM, e.g., by a point of care blood-glucose measurement device. The CGM is subsequently "recalibrated" with respect to the reference measurement. Upon receipt of a recalibrated data-point a recursive state estimator could update its state estimate as usual, or possibly employ a higher gain than when updating using CGM data, to reflect the higher confidence. A related approach was proposed in Kuure-Kinsey et al. [2006] for glucose estimation based on Kalman filtering, and such approaches appear to work well for the purpose of glucose estimation. However, for the purpose of state initialization in MPC the strategy is not ideal, because after a recalibration the state estimator undergoes a period of lively dynamics. These energetic responses may result in meaningless predictions that can lead to serious over-delivery. Thus, in our controllers, large recalibrations are followed by a period where the insulin infusion rate is constrained to the patient's basal rate. This seems wasteful, as a recalibration is the introduction of high-fidelity data into the system. Preferably the system could exploit this data and perform better after a recalibration, not have to undergo intentional, temporary crippling.

The second weakness is that asynchronous CGM data cannot be accommodated in current, recursive state estimators, where "asynchronous" means both that the sample-period of the CGM may not be fixed, and furthermore that the time-instants the CGM and controller perform updates may not be equal. Our controllers (both physical controller and discrete-time prediction model) are based on a T=5 min sample-period. Typical CGMs have the same sample-period, much of the time. However, CGMs may delay their output during times of high uncertainty. Also, communication disruptions between sensor and meter cause delayed measurement updates, only once data-transfer is reestablished. A state estimator based on a fixed sample-period may over-estimate the rate of change of the data if the actual sample-period is elongated, and not compensate for the delay between controller update times and the latest CGM measurements. Both issues cause MPC predictions that are initialized in such a way that they veer off the CGM trajectory, possibly resulting in inappropriate insulin delivery.

The third weakness is that due to plant-model mismatch, model-based recursive state estimators cannot always achieve offset-free estimates, even in steady-state, when the state is not admissible with respect to the model, input, and measured output. Offsets can be partially remedied by increasing the estimator gain, but this undesirably results in increased responsiveness to high-frequency noise.

We provide a state estimation strategy that tackles the aforementioned three weaknesses. Our solution is based on moving-horizon optimization and is not a recursive estimator. It is inspired by, but not equal to, the common notion of moving-horizon estimation (Rawlings and Mayne [2009]). The disclosed method performs optimization to fit a continuous-time function to the CGM data. Sensor recalibrations are accommodated straightforwardly by including a discontinuity in the glucose output value, but not its derivatives, within the function definition. Importantly, the magnitude of the discontinuity need not be prescribed, but is identified by the optimization. The data fitting exploits the CGM time-stamps and controller call time, thus asynchronous data sampling is handled naturally. After optimization the fitted function is sampled at exactly the controller model's sample-period T, ignoring the recalibration discontinuity, to synthesize an output trajectory. In combination with historical input data, and assuming observability, the current model state is constructed to reflect the fitted output trajectory without offset. The disclosed strategy can be combined with a Kalman filter, or other signal processing technique, to pre-treat the CGM data; however, for brevity, the exemplification is based on the use of raw CGM data.

SUMMARY OF THE INVENTION

A key component in a successful artificial pancreas system designed to maintain the blood glucose concentrations of people with type 1 diabetes mellitus within the euglycemic zone (80-140 mg/dL) is the control algorithm that automatically directs the delivery of insulin to be administered to a subject with type 1 diabetes. There are many varieties of control algorithm; this invention is applicable to classes of control strategies based on either "state-feedback", or on models with "auto-regressive" components, with particular emphasis on "model predictive control" algorithms Our artificial pancreas research group has designed and tested various state-feedback model predictive control strategies for use in an artificial pancreas for treating type 1 diabetes.

In one aspect the invention characterizes either a model state (for state-feedback controllers), or a model output trajectory (for auto-regressive model-based controllers), based on blood glucose measurements, for a controller to base its computations on, in order to facilitate superior control of blood glucose levels. Blood glucose measurements, obtained from currently available blood glucose sensors, have properties that cause current mechanisms for characterizing a model state to result in degraded, or inappropriate, control action. One implementation of the invention is; 1) to accommodate blood glucose sensor recalibrations, to facilitate superior control when the sensor is recalibrated; 2) to exploit time-stamps of the sensor measurements, to facilitate superior control when sensor measurements suffer from irregular sampling intervals; 3) to exploit the controller time-stamps, in addition to measurement time-stamps, to facilitate superior control when the controller and sensor update times are not synchronized. Furthermore, in contrast to existing techniques, the invention does not rely on a model, thus remedies undesirable effects due to inevitable plant-model mismatches.

The invention can be employed with any feedback control strategy based on either state-feedback, or auto-regressive models. The reason for its particular relevance to model predictive control algorithms is that, because a predictive controller's action is based on entire predicted trajectories, in contrast to solely the current model state, the need to appropriately initialize the model state is of increased priority. Simply stated, with predictive control it is required to set-off predictions pointing in the right direction.

In an aspect the invention functions by applying a continuous-time function fit to the obtained blood glucose sensor measurements, and subsequently sampling the fitted, continuous-time function at the model's sample-period, in order to synthesize a model output trajectory. That way the effects of asynchronous and inconsistent sensor timing are eradicated. Sensor recalibrations are accommodated by including a discontinuity in the value, but not derivatives, of the fitted function, at those instants in time that a recalibration occurs. Importantly, the discontinuity is disregarded during the sampling procedure. For state-feedback control the current model state is constructed from the synthesized output trajectory, in conjunction with the saved, historic values of the control input trajectory. For controllers based on auto-regressive models the synthesized model output trajectory may be employed directly, instead of the actual output trajectory as is currently the standard procedure.

The invention provides a state-initialization algorithm that can be incorporated into a device or algorithm that performs state-feedback model predictive control, for optimizing insulin delivery to type 1 diabetic people, based on blood glucose measurement feedback, e.g., in insulin pumps, continuous glucose monitoring systems, or an artificial pancreas.

The invention was evaluated on the Univ. Padova/Virginia FDA accepted metabolic simulator, and on clinical data of unrelated studies, and extended in silico and clinical trials, implementation as part of artificial pancreas, CGM devices or insulin pumps. The invention improves the capabilities of an artificial pancreas that uses model predictive control based on blood glucose measurements as feedback, in maintaining the blood glucose levels of people with type 1 diabetes mellitus within euglycemic range (80-140 mg/dL).

The invention operates to assure that control algorithms for artificial pancreases are using accurate past data points to make future calculations, works with any MPC control algorithm, and can provide an alarm system in open loop continuous glucose monitoring.

The invention encompasses various further aspects.

In one aspect the invention provides a method of state-estimator for the estimation or initialization of the state of a discrete-time state-space dynamical model based on sensor measurements of the model output, comprising fitting a continuous-time function to acquired sensor measurement data-points of each model output, and subsequently sampling the continuous time function at exactly the sample-period of the state-space dynamic model for which the state is being estimated or initialized, in order to construct a model state via a synthesized output trajectory; wherein (a) sensor re-calibrations are included, by permitting the fitted function to be discontinuous in its value, but not its derivatives, at the point of re-calibration, and wherein the magnitude of the discontinuity is identified by the optimization, and wherein the sampling of the fitted function is performed ignoring the re-calibration discontinuity;

(b) the function fit employs sensor measurement time-stamps and the state-estimator call-time, wherein:
  (i) delays between the sensor and state-estimator are at least partially mitigated by sampling the fitted function backwards in time starting at exactly the estimator call time; and
  (ii) sensor data collected at irregular time-intervals, or time-intervals that are not the sample-period of the model for which the state is being estimated or initialized, can be accommodated;

(c) the model for which the state is being estimated or initialized may have inputs, and if inputs are present historical input data is employed in construction of the state;

(d) the state of the model is observable or reconstructible;

(e) when the model for which the state is being estimated or initialized has one single output then the current model state is constructed to reflect the synthesized output trajectory without offset, and when the model for which the state is being estimated or initialized has multiple outputs then a trade-off strategy is employed to reconcile mismatching outputs.

This and other aspects may be further defined by various particular embodiments, such as:

wherein the sensor measurement data is pretreated with a Kalman filter or other signal processing technique;

wherein the method is deployed in automated drug delivery in biomedical applications, such as for type 1 diabetes, or process control implementations;

wherein the sensor is a continuous glucose monitor (CGM) and the discrete-time state-space dynamical model is employed for predicting blood glucose concentrations;

wherein the method is operatively combined with a state-feedback control law, such as a state-feedback model predictive control (MPC) law, to perform algorithmic insulin dosing;

wherein the method is operatively combined with a state-feedback control system, such as a state-feedback model predictive control (MPC) system, to deliver insulin;

wherein the method is operatively combined with an alarm and/or notification system, wherein the alarm and/or notification decision-making algorithm employs predictions, such as blood glucose predictions, performed by a discrete-time state-space dynamical model that uses the state of a model in its alarm and/or notification decision-making algorithm; and/or wherein the method is adapted for medical device control of drug delivery, such as a device adapted for a chronic medical condition or treatment, such as blood pressure control, hemodialysis control, anesthesia (e.g., depth of) control, Parkinson's treatment, leukemia treatment, cancer treatment, HIV treatment.

In another aspect the invention provides a method for controlling insulin delivery for treating type 1 diabetes mellitus, the method comprising using moving-horizon optimization to fit a continuous-time function to continuous glucose monitoring (CGM) data, wherein:

(a) sensor recalibrations are accommodated by including discontinuity in the glucose output value, but not its derivatives, within the function definition, and wherein the magnitude of the discontinuity is identified by the optimization;

(b) data fitting employs the CGM time-stamps and controller call time, thus asynchronous data sampling is handled naturally;

(c) after optimization the fitted function is sampled at the controller model's sample-period T, ignoring the recalibration discontinuity, to synthesize an output trajectory; and (d) in combination with historical input data, and assuming observability, the current model state is constructed to reflect the fitted output trajectory without offset.

In another aspect the invention provides a method for moving-horizon state-initializer for control of an insulin delivery controller of artificial pancreas for type 1 diabetes applications comprising:

constructing a state for a model by first fitting a function through acquired continuous glucose monitoring (CGM) data-points, then sampling the function at exactly the sample-period of the model for which the state is being estimated, wherein:

(a) CGM sensor re-calibrations are included, by permitting the fitted function to be discontinuous;

(b) delays between the sensor and controller are at least partially mitigated;

(c) data collected at irregular time-intervals, or a time-interval that is not the sample-period of the model for which the state is being estimated, can be accommodated; and (d) the model is not employed during or within the estimation process, rather the state is estimated for the model, wherein any plant-model mismatch affect on the final result is limited.

In another aspect the invention provides a method for model predictive control (MPC) of an artificial pancreas to treat Type 1 diabetes mellitus, comprising employing state estimation with sensor recalibrations and asynchronous measurements, wherein a state is constructed by output data synthesized by sampling a continuous-time function, where the function is characterized by fitting to measured continuous glucose monitoring (CGM) sensor data and including a discontinuity in the value, but not the derivatives, at time-instants of sensor recalibration.

The various aspects may be practiced or implemented in additional embodiments, including:

wherein the method is combined with a Kalman filter, or other signal processing technique, to pre-treat the CGM data;

the method is operatively combined with a model predictive control (MPC) control algorithm to deliver a drug, like insulin; and/or the method is operatively combined with an alarm system, such as for open loop CGM.

The invention also provides controllers programmed to implement a subject method, and drug delivery systems comprising a controller programmed to implement a subject method, optionally comprising a status monitoring system, a drug pump or metering system, and/or a drug to be delivered.

The invention includes algorithms and drug directing systems essentially as described herein, and all combinations of the recited particular embodiments. All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

DESCRIPTION OF PARTICULAR EMBODIMENTS OF THE INVENTION

Figure 1:
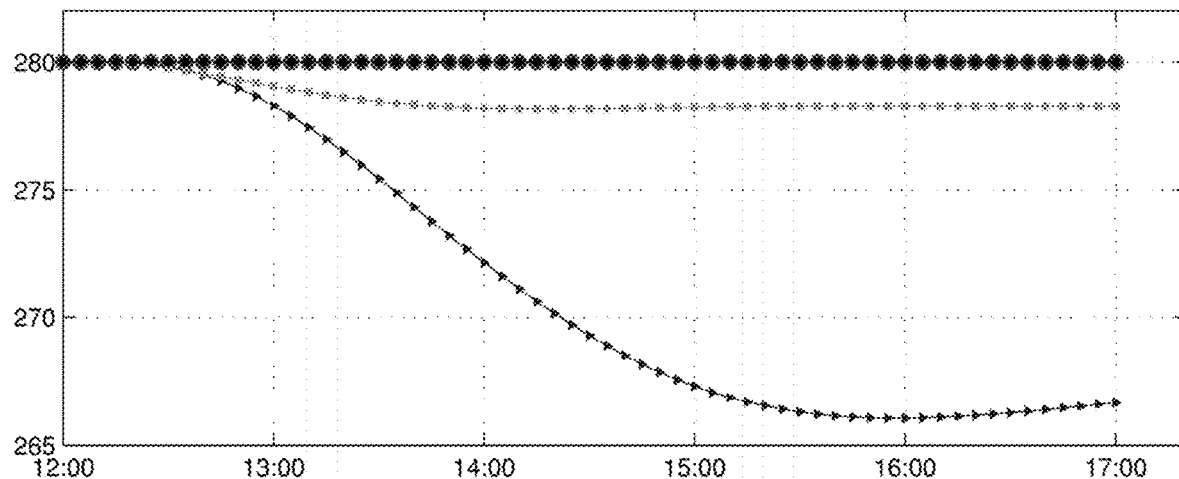
FIG. 1. Demonstration of plant-model mismatches. Glucose [mg/dL] v. Time of day [h]. CGM=280 mg/dL (large dots). Low-gain linear estimator (triangles). High-gain linear estimator (squares). Disclosed estimator (black dots).

State Estimation with Sensor Recalibrations and Asynchronous Measurements for MPC of an Artificial Pancreas to Treat T1DM A novel state estimation scheme is provided for use in Model Predictive Control (MPC) of an artificial pancreas based on Continuous Glucose Monitor (CGM) feedback, for treating type 1 diabetes mellitus. The performance of MPC strategies heavily depends on the initial condition of the predictions, typically characterized by a state estimator. Commonly employed Luenberger-observers and Kalman-filters are effective much of the time, but suffer limitations. Three particular limitations are addressed by our approach. First, CGM recalibrations, step changes that cause highly dynamic responses in recursive state estimators, are accommodated in a graceful manner Second, the disclosed strategy is not affected by CGM measurements that are asynchronous, i.e., neither of fixed sample-period, nor of a sample-period that is equal to the controller's. Third, the provision suffers no offsets due to plant-model mismatches. The provided approach is based on moving-horizon optimization.

Designs; Linear Time-Invariant Insulin-Glucose Model

The insulin-glucose model of van Heusden et al. [2012] is employed and is summarized as follows. The model is a discrete-time, Linear Time-Invariant (LTI) system with sample-period T=5 min [min]. The time step index is denoted by i. The scalar plant input is the administered insulin bolus $u_{IN,i}$ [U] delivered per sample-period, and the scalar plant output is the subject's blood-glucose value $y_{BG,i}$ [mg/dL]. The plant is linearized around a steady-state, that is assumed to be achieved by applying the subject-specific, time-dependent basal input rate $u_{BASAL,i}$ [U/h], and is assumed to result in a steady-state blood-glucose output $y_s$=110 [mg/dL].

The LTI model's input $u_i$ and output $y_i$ are defined as:

$$u_i := u_{IN,i} - u_{BASAL,i} \frac{T}{60 \text{ min}}$$

$$y_i := y_{BG,i} - y_s.$$

We denote by $z^{-1}$ the backwards shift operator, by $Y(z^{-1})$ and $U(z^{-1})$ the z-transform of the time-domain signals of input $u_i$ and output $y_i$, respectively. The transfer characteristics from u to y are described by $$\frac{Y(z^{-1})}{U(z^{-1})} = \frac{1800 \, Fc}{u_{TDI}} \frac{z^{-3}}{(1-p_1 z^{-1})(1-p_2 z^{-1})^2} \qquad (1)$$

with poles $p_1$=0.98, $p_2$=0.965, a so-called safety factor F=1.5 (unitless, personalizable but fixed to 1.5 throughout this paper), the subject specific total daily insulin amount $u_{TDI} \in \mathbb{R}_{>0}$ [U], and where the constant $$c := -60(1-p_1)(1-p_2)^2 \in \mathbb{R}$$

is employed to set the correct gain, and for unit conversion. The 1800 term stems from the "1800 rule" for estimating blood-glucose decline with respect to the delivery of rapid-acting insulin (Walsh & Roberts [2006]).

The state-space realization of (1) for control synthesis is $$x_{i+1} = Ax_i + Bu_i \qquad (2a)$$

$$y_i = Cx_i \qquad (2b)$$

$$A := \begin{bmatrix} p_1 + 2p_2 & -2p_1 p_2 - p_2^2 & p_1 p_2^2 \\ 1 & 0 & 0 \\ 0 & 1 & 0 \end{bmatrix} \in \mathbb{R}^{n \times n}$$

$$B := \frac{1800 \, Fc}{u_{TDI}} [1 \; 0 \; 0]^T \in \mathbb{R}^n$$

$$C := [0 \; 0 \; 1] \in \mathbb{R}^{1 \times n}$$

$$n = 3.$$

Let $O:=[C^T (CA)^T (CA^2)^T]^T \in \mathbb{R}^{n \times n}$, and note that O is equal to the identity matrix flipped top-to-bottom.

Remark 1: $\det(O) \neq 0$, i.e., (A, C) is observable.

Nominal Model Predictive Control Outline

For background on MPC, see: Rawlings and Mayne [2009]. Let $\mathbb{Z}$ denote the set of integers, $\mathbb{Z}_+$ the set of positive integers, and $\mathbb{Z}_a^b$ the set $\{a, \ldots, b\}$ of consecutive integers from a to b. Let $N \in \mathbb{Z}_+$ denote the prediction horizon, and u and x the predicted values of input u and state x. Then, MPC performs closed-loop control by applying, at each step i, the first control input $u^*_0$ of the predicted, optimal control input trajectory $\{u^*_0, \ldots, u^*_{N-1}\}$, characterized by the minimization $$\{u_0^*, \ldots, u_{N-1}^*\} := \arg \min_{\{u_0, \ldots, u_{N-1}\}} J(x_i, \{u_0, \ldots, u_{N-1}\}) \qquad (3)$$

of a suitable cost function $J(\cdot, \cdot)$ (details omitted for brevity), subject to suitable constraints, and furthermore subject to the predictions performed employing model (2):

$$x_0 := x_i, x_{k+1} := Ax_k + Bu_k \; \forall k \in \mathbb{Z}_0^{N-1}. \qquad (4)$$

The predicted state trajectory is initialized in (4) to the estimated model state, the value of which profoundly affects the performance of the resulting MPC control law. No notational distinction between actual and estimated state is made, because state x of (2) can only be estimated.

Controller timing and input history. The sample-period of (2), and the time interval between controller updates of control input u, are assumed to be the same and equal to T. For simplicity we further assume any controller employing model (2) to have access to the exact control input history, where previous control inputs $u_i$ were applied at time intervals of exactly T. We denote the actual time instants of the controller call by $\tau_i = \tau_{i-1} + T$.

Sensor timing, sensor recalibration, and output history. Each measurement is defined by a triple $(\tilde{y}_j, t_j, r_j)$, where $j \in \mathbb{Z}_+$ denotes the measurement index that is incremented with each new measurement, $\tilde{y}_j \in \mathbb{R}$ denotes the CGM output, analogous to y of (2b) (i.e., with set-point $y_s$ subtracted), as provided by the CGM at time-instant $t_j$. The variable $r_j \in \mathbb{Z}$ denotes a recalibration counter, and is incremented each time the sensor is recalibrated ($r_j := 0$).

The time interval between successive measurements may not be precisely T. However, we suppose that $t_j - t_{j-1} < 2T$ for all j. Analogously, we assume the time interval between a controller call at $\tau_i$, and the most recent measurement at $t_i$, to be less than 2T. If the interval exceeds two sample-periods then, for an interval of a low multiple of sample-periods, a strategy employing open-loop predictions of model (2) to "fill the gap" may be useful. For simplicity such scenarios are not considered here, although they are in the clinical controller implementations.

Each output measurement $\tilde{y}_i$ at time $t_i$ suffers from errors due to process noise and measurement noise. However, CGM noise has proven difficult to model accurately (Hovorka [2006]), thus in this work we make no assumptions about the measurement errors, and include in the state-estimation scheme no strategy for exploiting perceived knowledge of the noise characteristics. However, we assume that measurements $\tilde{y}_j$ such that $r_j \neq r_{j-1}$ are exact, because r is incremented when the sensor is recalibrated. The disclosed state-estimation strategy achieves rejection of high-frequency disturbances to some (tunable) extent, but even without recent sensor recalibrations, the disclosed strategy estimates the state under the assumption that the low-frequency measurement bias is zero.

State-reconstruction based on exact outputs and inputs. We denote by $I_a$ the $a \times a$ identity matrix, by $0_{\{a,b\}}$ the $a \times b$ zero matrix, and by $\otimes$ the Kronecker product.

At each step i, given the exact sequence $\{y_k\}_{k=i-n+1}^{i}$ of past outputs (and present), synchronized to the controller timing $\tau_i = \tau_{i-1} + T$, and further given the exact sequence $\{u_k\}_{k=i-n+1}^{i-1}$ of past control inputs, the current state $x_i$ of model (2) may be reconstructed, e.g., as follows. Let $$U_i := [u_{i-n+1} \ldots u_{i-1}]^T \in \mathbb{R}^{n-1} \quad (5)$$

$$Y_i := [y_{i-n+1} \ldots y_i]^T \in \mathbb{R}^n$$

$$X_i := [x_{i-n+1}^T \ldots x_i^T]^T \in \mathbb{R}^{n^2}$$

$$\bar{A} := [I_n \ A^T \ (A^{n-1})^T]^T \in \mathbb{R}^{n^2 \times n}$$

$$\hat{A} := \begin{bmatrix} 0 & 0 & \ldots & 0 \\ I_n & 0 & \ldots & 0 \\ A & I_n & \ldots & 0 \\ \vdots & \vdots & \ddots & \vdots \\ A^{n-2} & A^{n-3} & \ldots & I_n \end{bmatrix} \in \mathbb{R}^{n^2 \times n(n-1)}$$

$$\bar{B} := \hat{A}(I_{n-1} \otimes B) \in \mathbb{R}^{n^2 \times (n-1)}$$

$$\bar{C} := (I_n \otimes C) \in \mathbb{R}^{n \times n^2}$$

$$F := [0_{\{n, n(n-1)\}} \ I_n] \in \{0, 1\}^{n \times n^2}$$

such that $$X_i = \bar{A} x_{i-n+1k} + \bar{B} U_i$$

$$Y_i = \bar{C} X_i \quad (6)$$

$$x_i = F X_i \quad (7)$$

where at step i all except $X_i$ are known. From (5) and (6):

$$x_{i-n+1} = (\overline{CA})^{-1}(Y_i - \overline{CB} U_i). \quad (8)$$

The current state $x_i$ is then characterized via (5) and (7). The inverse in (8) exists by Remark 1, because $\overline{CA} = O$.

State-Estimation via Output Trajectory Fitting. At each step i the parameter $\theta_i \in \Theta$ defining a continuous-time function $f: \mathbb{R} \times \Theta \to \mathbb{R}$ is identified such that it closely fits recent data-points. The continuous-time function $f(t, \theta_i)$ is subsequently sampled at time instants $\tau_k$, $k \in \mathbb{Z}_{i-n+1}^{i}$ to synthesize a trajectory $\{\hat{y}_k\}_{k=i-n+1}^{i}$ of synchronous, past (and one present) output values. This manufactured output trajectory is employed, in conjunction with the exact sequence $\{u_k\}_{k=i-n+1}^{i-1}$ of past control inputs, to construct an estimate of the current state $x_i$ by the mechanism as described herein.

The function fitting is performed using unconstrained least-squares fitting of polynomials. More general cost functions, more general functions $f(\cdot)$, and also constraints, could be considered, but these complexities are dispensed with here to focus on the advantages in terms of timing and sensor recalibrations. A benefit, with regards to timing and the asynchronous nature of the CGM data-points, is that the function fitting can be performed with data-points that are temporally distributed in an arbitrary way. An important, novel functionality with respect to sensor recalibrations is that due to the optimization-based nature (in contrast to recursive estimators) a discontinuity can be accommodated when a recalibration occurs. The discontinuity's size need not be known, but is identified from the data via the optimization. Assuming that at most one recalibration occurred in the near history, the discontinuity is included when fitting data points prior to recalibration, but is not included when fitting more recent data-points. Critically, the discontinuity is not included when sampling $f(\cdot)$ to synthesize the fabricated output trajectory of $\hat{y}$ values.

The optimization penalizes the deviation $\theta_i - \theta_{i-1}$ of the parameter from one step to the next, thus introducing a "viscosity" for rejecting high-frequency disturbances.

Data Fitting with Function Discontinuity

For consistent interpretation of the value of parameter $\theta_i$ as i progresses, the function $f(\cdot)$ is fitted shifting the current time $\tau_i$ to the origin. The class of continuous-time functions considered for fitting is the p-order polynomial $$f(t, \theta_i) := \sum_{k=0}^{p} a_{(i,k)}(t - \tau_i)^k = [1 \ (t - \tau_i) \ \ldots \ (t - \tau_i)^p] \theta_i \quad (9)$$

$$a_{(i,k)} \in \mathbb{R} \ \forall \ (i, k) \in \mathbb{Z} \times \mathbb{Z}_0^p$$

$$\theta_i := [a_{(i,0)} \ \ldots \ a_{(i,p)}]^T \in \mathbb{R}^{p+1},$$

where p is a design parameter. Let the design parameter $M \in \mathbb{Z}_+$ denote a length of measurement history to consider. For each step i, let $c_i \in \mathbb{Z}_+$ denote the index of the most recent measurement, and let $d_i \in \mathbb{Z}_{c_i - M + 1}^{c_i}$ denote the index of the most recent measurement that followed a sensor recalibration. The range specified for d implies that a recalibration occurred within the M-length history horizon. The case when the latest recalibration occurred prior to the M-length history horizon is simple and not discussed further. For simplicity we do not discuss the case with multiple recalibrations within the history horizon M, although such cases can be accommodated.

The At step i, the measurements employed for state estimation are $(\tilde{y}_j, t_j, r_j)$, $j \in \mathbb{Z}_{c_i - M + 1}^{c_i}$. It holds that $r_i = r_j + 1 \forall$ $(i, k) \in \mathbb{Z}_{d_i}^{c_i} \times \mathbb{Z}_{c_i - M + 1}^{d_i - 1}$. Let $\delta_i \in \mathbb{R}$ denote the (unknown) size of measurement discontinuity resulting from a recalibration, and define the augmented parameter $\bar{\theta}_i := [\delta_i, \theta_i^T]^T \in \mathbb{R}^{p+2}$. Denote the error, between the discontinuous fitted function and the data, as follows:

$$e_{(i,j)} := \begin{cases} \tilde{y}_j - [1 \ 0 \ (t_j - \tau_i) \ \ldots \ (t_j - \tau_i)^p] \bar{\theta}_i & \text{if } j \in \mathbb{Z}_{d_i}^{c_i} \\ \tilde{y}_j - [1 \ 1 \ (t_j - \tau_i) \ \ldots \ (t_j - \tau_i)^p] \bar{\theta}_i & \text{otherwise} \end{cases}.$$

Let $R_k \in \mathbb{R}_{>0} \forall k \in \mathbb{Z}_1^M$ denote costs to penalize errors $e_{(i,j)}$, time-dependent with respect to relative time the measurement was taken, but not time-dependent with respect to actual time. Further let $Q_i \in \mathbb{R}^{(p+1) \times (p+1)}$, $Q_i \succcurlyeq 0$ denote a cost for penalizing parameter deviations $\theta_i - \theta_{i-1}$. The optimal augmented parameter $\bar{\theta}^*_i$ is characterized by the solution of the following quadratic program:

$$\bar{\theta}^*_i := \arg\min_{\bar{\theta}_i \in \mathbb{R}^{p+2}} (\theta_i - \theta^*_{i-1})^T Q_i (\theta_i - \theta^*_{i-1}) + \sum_{k=1}^{M} R_k e^2_{(i, c_i - k + 1)}.$$

The cost $R_k$ should, in general, be chosen such that $R_k \geq R_{k+1}$, i.e., such that more recent measurements influence the optimal parameter estimate $\theta^*_i$ more than older ones. The cost matrix $Q_i$ is chosen to penalize parameters $a_{(i,k)}$ of (9), and should generally be diagonal. A higher cost allows to set a "viscosity" on the rate of change of, e.g., the value via $Q_{(1,1)}$, or the velocity via $Q_{(2,2)}$, etc. Note that after a recalibration it is desirable to select $Q_{(1,1)}=0$ in order to facilitate an instantaneous response to the recalibration step change.

Output Trajectory Manufacture

Given the optimized parameter $\theta^*_i$, the synthesized output trajectory, employed for constructing the estimated state via the method described herein, is defined by sampling the function $f(t, \theta^*_i)$ at times $t \in \{0, -T, -2T, \ldots\}$.

Illustrative Examples

In this section the behavior and benefits of the disclosed state estimation strategy are demonstrated by simple, numerical examples. The parameter choices were made to produce the simplest, within reason, instance of the disclosed strategy. The order $p=1$ of the polynomial of (9) is employed, i.e., we perform a straight-line fit. Note that the number of data-points M employed must equal, or exceed, the degrees of freedom of the function fitting. Thus we select a history horizon M=3, facilitating a straight-line fit with one recalibration. We let $R_1 = R_2 = 1$ and $R_3 = 0.1$, to penalize the error w.r.t. the eldest data-point less than the error associated with the most recent two data-points. Finally, we select $Q = 0_{\{2,2\}}$, i.e., the optimal parameter $\theta^*_i$ is independent of the previous step's $\theta^*_{i-1}$.

We compare the responses of the disclosed state estimator with a linear state estimator that is based on model (2):

$$\tilde{x}_i = A x_{i-1} + B u_{i-1}, \tilde{y}_i = C \tilde{x}_i \quad (10a)$$

$$x_i = \tilde{x}_i + L(y_i - \tilde{y}_i). \quad (10b)$$

Rejection of Plant-Model Mismatches

FIG. 1 demonstrates how the gain L of a linear state estimator affects the ability to reject plant-model mismatches. The CGM is constant at 280 mg/dL, and insulin infusion is performed at the basal-rate. A higher gain L rejects mismatches more effectively, but results in elevated responsiveness to noise. Note that, in this example, the linear state estimator's state is initialized to achieve the CGM value in steady state. Despite this optimal initialization, the linear state estimator's state estimate drifts, inducing a steady state mismatch in estimator output $C x_i$ and the CGM signal. The reason for this is that model (2) is based on linearization around $y_s = 110$ mg/dL, and that the elevated, steady-state CGM value is not compatible with the basal insulin delivery. In contrast, the disclosed state estimator suffers no such mismatches, because the synthesized output trajectory is manufactured based solely on the CGM data, not model (2), and because, by observability, the mechanism constructs a state that corresponds exactly to this fabricated output trajectory.

MPC & CGM Synchronized-Sample-Period Incorrect

In this example we demonstrate what happens when the CGM data is transmitted every 9 min instead of T=5 min, under the assumption that the controller updates simultaneously, only every 9 min. This is not how the MPC is implemented in practice (herein); nevertheless, the example is instructive.

Figure 2:
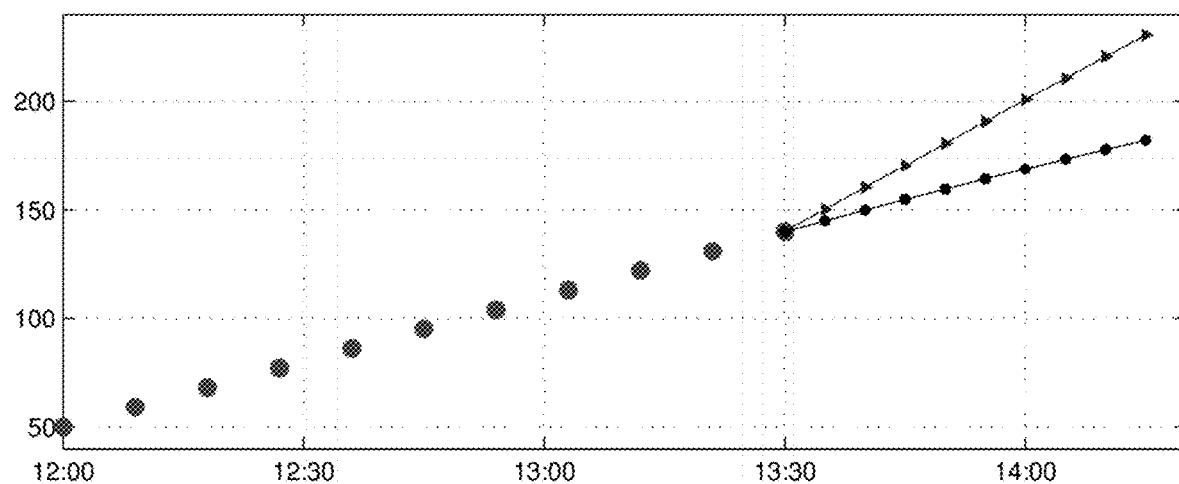
FIG. 2. Demonstration of elongated sample-period. Glucose [mg/dL] v. Time of day [h]. GCM and MPC synchronized. CGM (large dots) rate of increase: 1 mg/dL/min. Linear estimator-based MPC predictions (triangles). Disclosed estimator-based MPC predictions (black dots).

We consider a CGM trajectory that is rising at 1 mg/dL/min, sampled every 9 min The CGM data are recursively input to estimator (10), that is not able to exploit the data's time-stamps, because model (2) is based on a T=5 min sample-period. The gain L is chosen high, i.e., the estimator is responsive and the output error is rejected well. The result is depicted in FIG. 2. Despite achieving an accurate starting value for the output $C x_i$, the rate of change is clearly mis-initialized to an over-estimated value, and the MPC predictions veer away from the CGM trajectory. In contrast, the disclosed estimator exploits both the controller's call time and also the CGM time-stamps, and accounts for arbitrary timing in an appropriate manner. Based on the disclosed estimator's state the MPC predictions are a continuation of the CGM trajectory.

MPC & CGM Sample-Instants Offset

Figure 3:
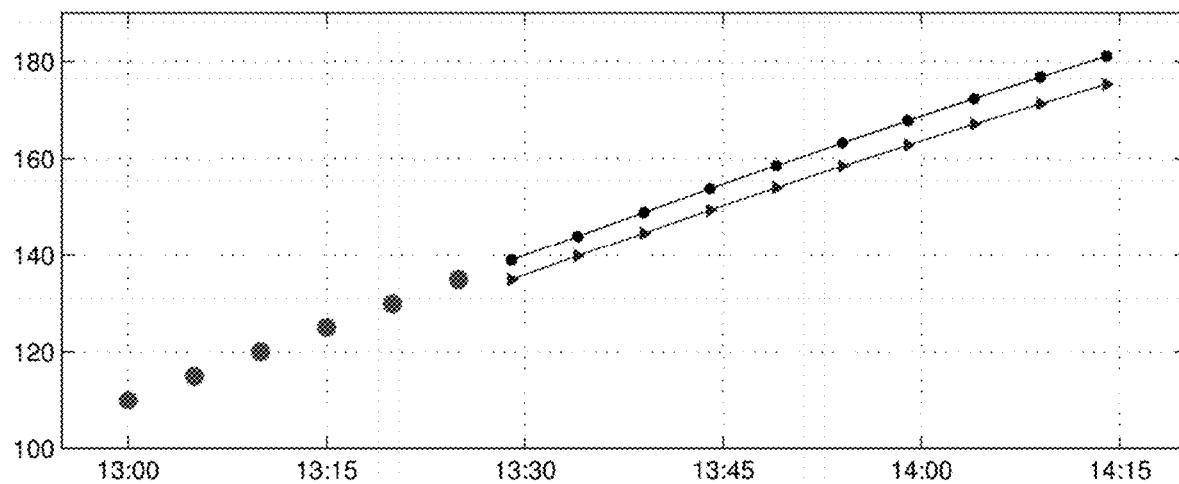
FIG. 3. Demonstration of 4 min delay between MPC update and CGM. Glucose [mg/dL] v. Time of day [h]. CGM (large dots) rate of increase: 1 mg/dL/min. Linear estimator-based MPC predictions (triangles). Disclosed estimator-based MPC predictions (black dots).

In this example we demonstrate the ability of the disclosed estimator to accommodate delays between the controller update time instants and the CGM. We consider a CGM trajectory with rate of change of 1 mg/dL/min, with a data-point every T=5 min. The controller updates every T=5 min, delayed by 4 mins w.r.t. the latest CGM value. The result is plotted in FIG. 3. Despite the delay the linear estimator causes the MPC predictions to start at the most recent CGM value. In contrast, the disclosed estimator initiates the MPC predictions from an extrapolated value lying on a continuation of the CGM data trajectory.

A benefit of the disclosed estimator, in regard to delay compensation, is negligible when the CGM's rate of change is low, which is most of the time. However, the CGM signal undergoes rapid change after, e.g., meal ingestion or the commencement of exercise. It is exactly at these challenging times that controller responsiveness is crucial.

MPC & CGM Asynchronous

In this example we consider the case were the controller updates the control input at a sample-period T=5 min, as intended. The CGM value rises at 1 mg/dL/min, but updates its value only every 7 mins. Due to this mismatch in sample-periods, MPC and CGM sometimes update simultaneously, often times there is a delay between them, and other times no CGM update occurred since the previous MPC update.

Figure 4:
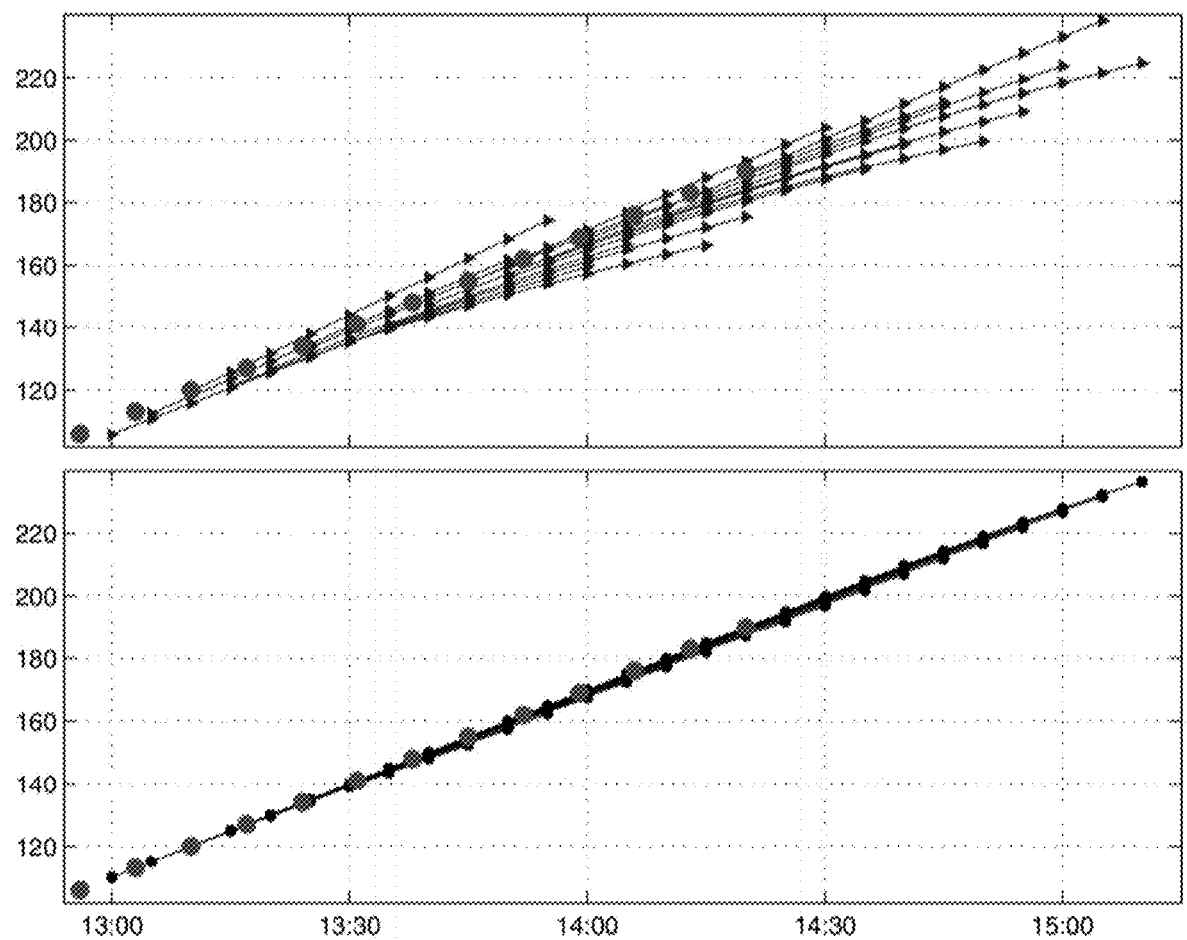
FIG. 4. Demonstration with MPC and CGM asynchronous. Glucose [mg/dL] v. Time of day [h]. MPC sample-period: 5 min. CGM sample-period 7 min. CGM (large dots) rate of increase 1 mg/dL/min. TOP: Linear estimator, MPC predictions (squares). BOTTOM: disclosed estimator, MPC predictions (black dots).

We consider a linear state estimator with high gain, updated with the most recent CGM value at each controller call. The resulting MPC predictions are depicted in the top subplot of FIG. 4. The predictions produce a feather-like spread around the CGM trajectory, where this spread is a result of both an offset in glucose value, as well as mis-initialization of the rate of change. In contrast, plotted in the bottom subplot of FIG. 4 are the MPC predictions when initialized by the disclosed estimator. The predictions overlay tightly. They do not overlap perfectly due to the controller tuning; the predictions veer slightly downwards due to the predicted delivery of insulin.

Recalibration

The initial motivation for the disclosed approach was to gracefully accommodate sensor recalibrations—demonstrated next. The controller and CGM are synchronized to the correct sample-period; T=5 min. The CGM reads 200 mg/dL until 14:25, is recalibrated to 250 mg/dL at 14:30, and remains at that reading thereafter.

Figure 5:
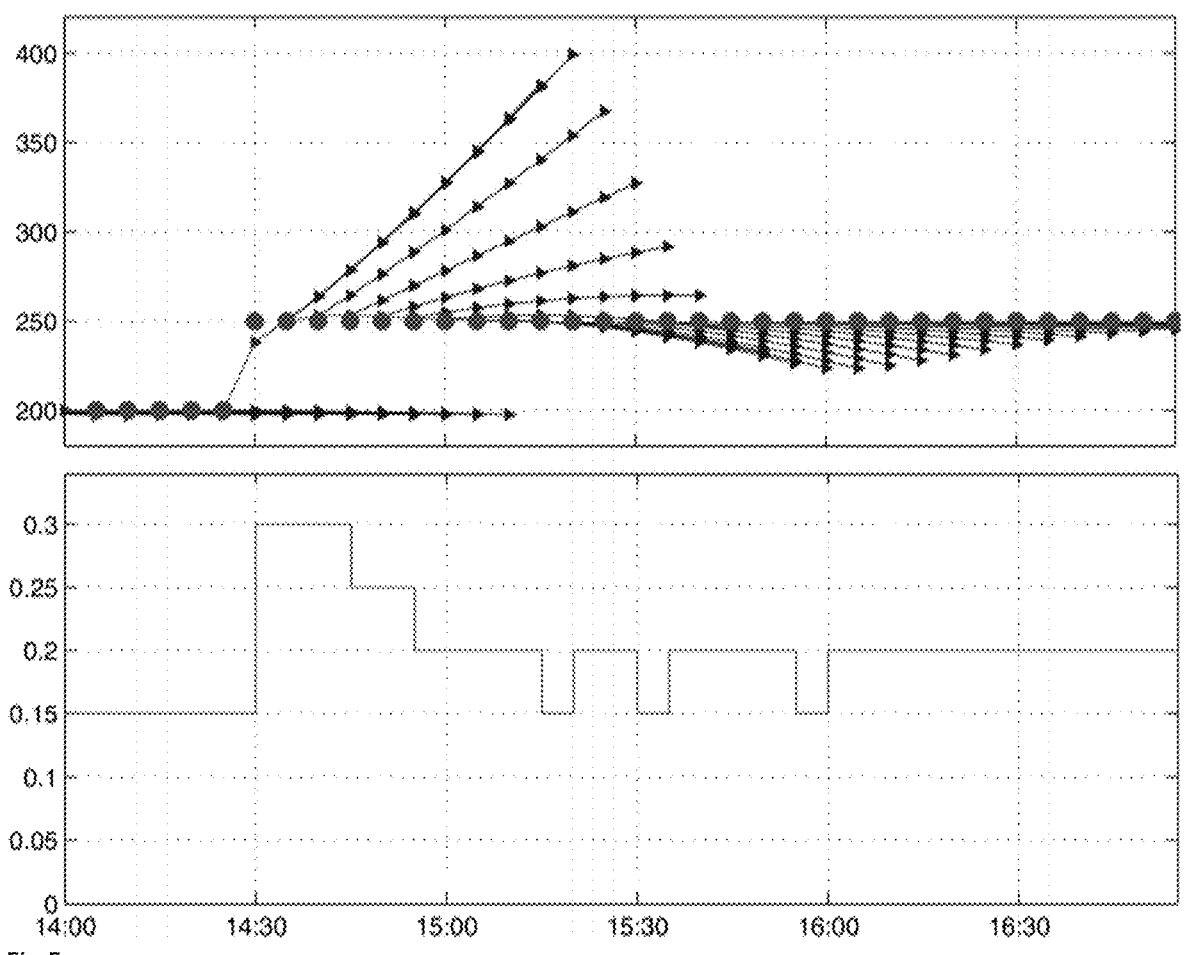
FIG. 5. Demonstration of recalibration response with linear state estimator and no safety features. Glucose [mg/dL] or Insulin [U/5 min] v. Time of day [h]. MPC and CGM synchronous: T=5 min CGM (large dots). MPC predictions (triangles). Estimated blood-glucose value (grey solid line).

The response with the linear state estimator is depicted in FIG. 5. Looking at the estimated blood-glucose level (grey line), it can be seen that the linear estimator performs admirably in terms of rapid convergence. The linear state estimator has a high gain, leading to a "forceful" correction of the estimator state x to produce an output Cx that equals the CGM value. However, such high gain estimation is inappropriate for initializing MPC predictions, due to the highly dynamic response of the predictions for a protracted period following the recalibration. This response in the state estimate causes a large, undesirable overshoot in the insulin delivery. A low gain linear state estimator may be more desirable for MPC state initialization here, resulting in predictions that have less incline and consequently a more conservative insulin delivery. However, a low gain estimator results in sluggish convergence to the correct glucose level and, depending on the glucose value, an offset due to plant-model mismatch.

Figure 6:
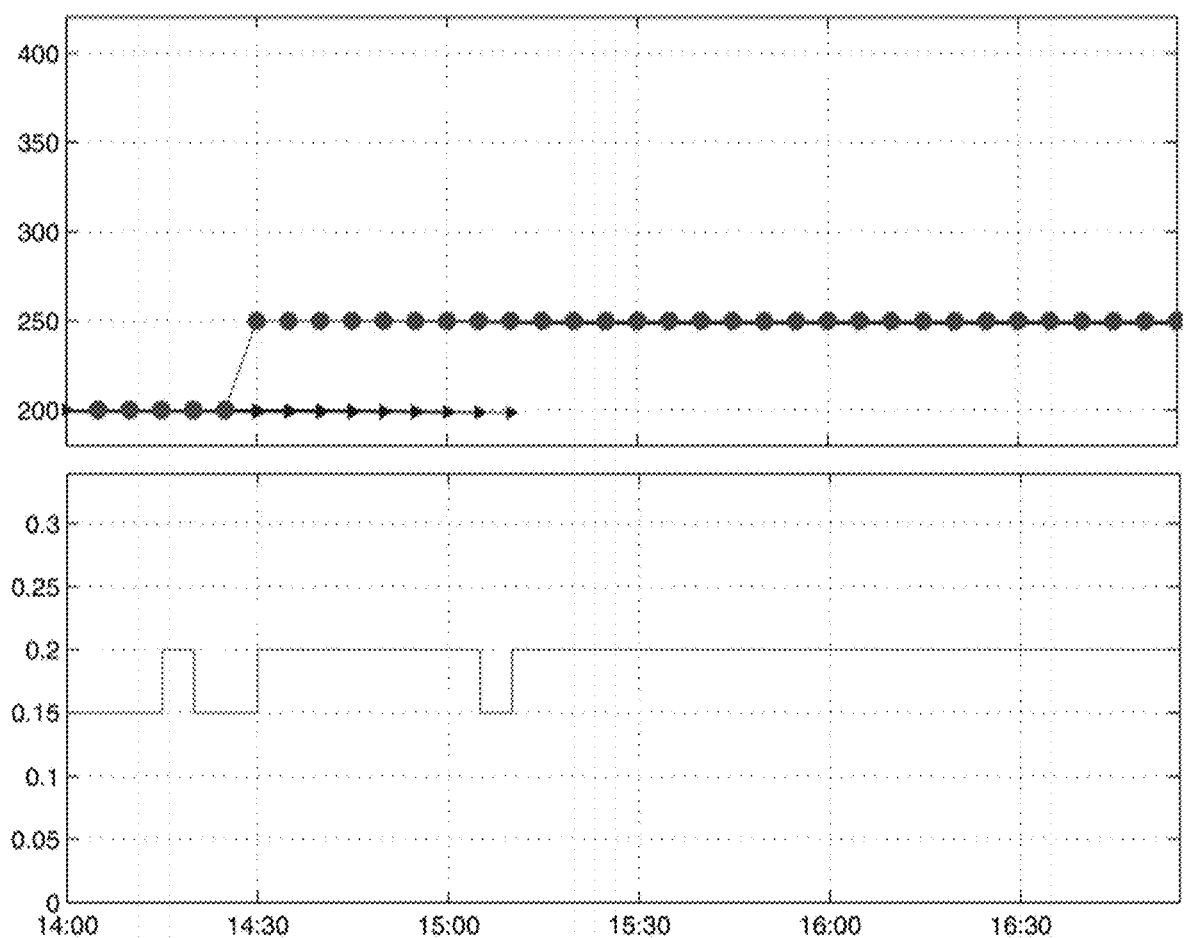
FIG. 6. Demonstration of recalibration response with disclosed state estimator and no safety features. Glucose

FIG. 6 shows the response with the disclosed estimator. The estimated glucose value instantaneously changes at 14:30 to the recalibrated value, and the state estimate instantaneously switches to a new value that, first, reflects the new CGM value, and, second, reflects the rate of change of the CGM trajectory in recent history. The MPC predictions beyond the recalibration are therefore nearly not visible. The resulting insulin delivery undergoes a step change upwards at the recalibration time instant. The two short-term deviations from steady-state delivery are due to the pump's discretization and carryover scheme. Both before and after the insulin step change a delivery in excess of the basal rate is desirable, due to the hyperglycemia. Thus, a safety mechanism that enforces basal delivery during the rapid transients of the state estimator would pose an obstacle to effective glucose control.

CONCLUSION

A novel state estimation scheme, based on moving-horizon optimization, is disclosed to solve problems associated with recursive state estimators for initializing MPC optimizations based on CGM data. The mechanics and benefit of the disclosed strategy were demonstrated using simple, synthetic examples. The disclosed method was tested via the University of Padova/Virginia FDA accepted metabolic simulator (Kovatchev et al. [2009]) and behaves comparably to a responsively tuned linear state estimator in "normal" circumstances, i.e., when not dealing with the problem instances that inspired the disclosure. When more challenging scenarios are simulated, the disclosed estimator's performance is verified with CGM data that more closely resembles that obtained in clinical trials.

The disclosed scheme offers a flexible foundation for extensions. (a) The disclosed method can be combined with, e.g., a Kalman filter, for tackling high-frequency noise, when far from a recalibration. (b) The disclosed method was described using polynomials as the fitting function, but Miller and Strange [2007] report that Fourier series are effective for fitting to CGM data. (c) Additional CGMs can provide data richer than only blood-glucose estimates, e.g., with accompanying estimates of confidence bounds. The optimization based approach offers an avenue to exploit such auxiliary information. (d) The notion of bias-control—the ability to manipulate the state estimate in a well-defined manner based on further sensors or user input—is facilitated, providing improved safety after detecting, e.g., a meal, exercise, a pump failure, or a sudden loss of CGM sensitivity.

REFERENCES

Bequette, B. W., Optimal Estimation Applications to Continuous Glucose Monitoring, In Proc. AACC American Control Conf., pages 958-962, Boston, Mass., USA, June 2004.

Breton, M, Farret, A, Bruttomesso, D, Anderson, S, Magni, L, Patek, S, Dalla Man, C, Place, J, Demartini, S, Del Favero, S, Toffanin, C, Hughes-Karvetski, C, Dassau, E, Zisser, H, Doyle III, F. J, De Nicolao, G, Avogaro, A, Cobelli, C, Renard, E, & Kovatchev, B., Fully Integrated Artificial Pancreas in Type 1 Diabetes: Modular Closed-Loop Glucose Control Maintains Near Normoglycemia, Diabetes, 61 (9):2230-2237, June 2012.

Cobelli, C, Dalla Man, C, Sparacino, G, Magni, L, De Nicolao, G, & Kovatchev, B. P., Diabetes: Models, Signals and Control, IEEE Rev. Biomed. Eng., 2:54-96, 2009.

Cobelli, C, Renard, E, & Kovatchev, B., Artificial Pancreas: Past, Present, Future, Diabetes, 60 (11):2672-2682, November 2011.

Doyle III, F. J, Huyett, L. M, Lee, J. B, Zisser, H. C, & Dassau, E., Bench to Clinic Symposia—Closed Loop Artificial Pancreas Systems: Engineering the Algorithms, Diabetes Care, 37:1191-1197, 2014.

Gondhalekar, R, Dassau, E, Zisser, H. C, & Doyle III, F. J., Periodic-Zone Model Predictive Control for Diurnal Closed-loop Operation of an Artificial Pancreas, J. Diabetes Sci. Technol., 7 (6):1446-1460, November 2013.

Gondhalekar, R, Dassau, E, & Doyle III, F. J., MPC Design for Rapid Pump-Attenuation and Expedited Hyperglycemia Response to Treat T1DM with an Artificial Pancreas, In Proc. AACC American Control Conf., Portland, Oreg., USA, pp. 4224-4230, June 2014.

Grosman, B, Dassau, E, Zisser, H. C, Jovanovic, L, & Doyle III, F. J., Zone Model Predictive Control: A Strategy to Minimize Hyper- and Hypoglycemic Events, J. Diabetes Sci. Technol., 4 (4):961-975, July 2010.

Grosman, B, Dassau, E, Zisser, H, Jovanovic, L, & Doyle III, F. J., Multi-Zone-MPC: Clinical Inspired Control Algorithm for the Artificial Pancreas, In Proc. 18th IFAC World Congress, pages 7120-7125, Milan, Italy, August 2011.

Harvey, R. A, Wang, Y, Grosman, B, Percival, M. W, Bevier, W, Finan, D. A, Zisser, H, Seborg, D. E, Jovanovic, L, Doyle III, F. J, & Dassau, E., Quest for the Artificial Pancreas: Combining Technology with Treatment, IEEE Eng. Med. Biol. Mag., 29 (2):53-62, 2010.

Hovorka, R., Continuous glucose monitoring and closed-loop systems, Diabetic Med., 23 (1):1-12, January 2006.

Hovorka, R, Canonico, V, Chassin, L. J, Haueter, U, Massi-Benedetti, M, Federici, M. O, Pieber, T. R, Schaller, H. C, Schaupp, L, Vering, T, & Wilinska, M. E., Nonlinear model predictive control of glucose concentration in subjects with type 1 diabetes. Physiol. Meas., 25:905-920, July 2004.

Kovatchev, B. P, Breton, M, Dalla Man, C, & Cobelli, C., In Silico Preclinical Trials: A Proof of Concept in Closed-Loop Control of Type 1 Diabetes, J. Diabetes Sci. Technol., 3 (1):44-55, January 2009.

Kuure-Kinsey, M, Palerm, C. C, & Bequette, B. W., A Dual-Rate Kalman Filter for Continuous Glucose Monitoring, In Proc. EMBS Annual Int. Conf., pages 63-66, New York City, N.Y. USA, August 2006.

Levine, W. S, editor., The Control Handbook, CRC Press, Boca Raton, Fla., USA, 2 edition, 2011.

Magni, L, Raimondo, D. M, Dalla Man, C, De Nicolao, G, Kovatchev, B, & Cobelli, C., Model predictive control of glucose concentration in type 1 diabetic patients: An in silico trial, Biomed. Signal Process. Control, 4 (4):338-346, 2009.

Magni, L, Raimondo, D. M, Bossi, L, Dalla Man, C, De Nicolao, G, Kovatchev, B, & Cobelli, C., Model Predictive Control of Type 1 Diabetes: An in Silico Trial, J. Diabetes Sci. Technol., 1 (6):804-812, November 2007.

Miller, M & Strange, P., Use of Fourier Models for Analysis and Interpretation of Continuous Glucose Monitoring Glucose Profiles, J. Diabetes Sci. Technol., 1 (5):630-638, September 2007.

Parker, R. S, Doyle III, F. J, & Peppas, N. A., A Model-Based Algorithm for Blood Glucose Control in Type I Diabetic Patients, IEEE Trans. Biomed. Eng., 46 (2):148-157, February 1999.

Rawlings, J. B & Mayne, D. Q., Model Predictive Control: Theory and Design, Nob Hill Publishing, Madison, Wis., USA, August 2009.

Turksoy, K, Bayrak, E. S, Quinn, L, Littlejohn, E, & Cinar, A., Multivariable Adaptive Closed-Loop Control of an Artificial Pancreas Without Meal and Activity Announcement, Diabetes Technol. Ther., 15 (5):386-400, May 2013.

van Heusden, K, Dassau, E, Zisser, H. C, Seborg, D. E, & Doyle III, F. J., Control-Relevant Models for Glucose Control Using A Priori, Patient Characteristics, IEEE Trans. Biomed. Eng., 59 (7):1839-1849, July 2012.

Walsh, J & Roberts, R., Pumping Insulin, Torrey Pines Press, San Diego, Calif., USA, 4 edition, 2006.

Zisser, H., Clinical Hurdles and Possible Solutions in the Implementation of Closed-Loop Control in Type 1 Diabetes Mellitus, J. Diabetes Sci. Technol., 5 (5):1283-1286, September 2011.

What is claimed is:

1. A method of state-estimator for estimation or initialization of state of a discrete-time state-space glucose dynamical controller model based on sensor measurements of output of the model, wherein the discrete-time state-space dynamical model is employed for predicting blood glucose concentrations, the method comprising:

receiving blood glucose sensor measurements from a continuous glucose monitor (CGM) sensor, the blood glucose sensor measurements including first sensor measurements before a recalibration of the sensor, and second sensor measurements after the recalibration of the sensor;

fitting a first function to the received first and second sensor measurements using moving-horizon optimization, the first function including a discontinuity at a time of the recalibration of the sensor;

determining a magnitude of the discontinuity;

shifting the first sensor measurements by an amount equal to the magnitude of the discontinuity;

fitting a second function to the shifted first sensor measurements and the second sensor measurements; and sampling the second function to generate an output trajectory, wherein:

sensor recalibrations are accommodated by including the discontinuity in a glucose output value, but not its derivatives, within the first function's definition, and wherein the magnitude of the discontinuity is identified by the optimization;

data fitting employs CGM time-stamps and controller call time;

after optimization the second function is sampled at the controller model's sample-period T, ignoring the recalibration discontinuity, to synthesize the output trajectory; and in combination with historical input data, and assuming observability, a current model state is constructed to reflect the output trajectory without offset.

2. The method of claim 1 wherein the sensor measurements are pretreated with a Kalman filter.

3. The method of claim 1 operatively combined with a state-feedback control system that is a state-feedback model predictive control (MPC) system, to deliver insulin.

4. The method of claim 1 operatively combined with an alarm system for open loop CGM.

5. The method of claim 1 operatively combined with a state-feedback control system that is a state-feedback model predictive control (MPC) system, to deliver insulin, and operatively combined with an alarm system for open loop CGM.

6. The method of claim 5 operatively combined with an alarm system for open loop CGM.

7. A controller programmed to implement a method of claim 1.

8. A controller programmed to implement a method of claim 2.

9. A controller programmed to implement a method of claim 3.

10. A controller programmed to implement a method of claim 4.

11. A controller programmed to implement a method of claim 5.

12. A controller programmed to implement a method of claim 6.

13. A controller programmed to implement a method of claim 1, and further comprising a status monitoring system.

14. A controller programmed to implement a method of claim 1, and further comprising an insulin pump or metering system.

15. A controller programmed to implement a method of claim 1, and further comprising insulin to be delivered.

16. A controller programmed to implement a method of claim 6, and further comprising a status monitoring system.

17. A controller programmed to implement a method of claim 6, and further comprising an insulin pump or metering system.

18. A controller programmed to implement a method of claim 6, and further comprising insulin to be delivered.

* * * * *